United States Patent
Buttaravoli

(10) Patent No.: US 10,610,656 B2
(45) Date of Patent: Apr. 7, 2020

(54) INTERMANDIBULAR/MAXILLARY VENTILATION DEVICE

(71) Applicant: Philip M Buttaravoli, West Palm Beach, FL (US)

(72) Inventor: Philip M Buttaravoli, West Palm Beach, FL (US)

(*) Notice: Subject to any disclaimer, the term of this patent is extended or adjusted under 35 U.S.C. 154(b) by 268 days.

(21) Appl. No.: 14/168,294

(22) Filed: Jan. 30, 2014

(65) Prior Publication Data
US 2014/0216470 A1   Aug. 7, 2014

Related U.S. Application Data

(60) Provisional application No. 61/759,601, filed on Feb. 1, 2013.

(51) Int. Cl.
| A61M 16/04 | (2006.01) |
| A61M 16/06 | (2006.01) |
| A61M 16/08 | (2006.01) |
| A61M 16/10 | (2006.01) |

(52) U.S. Cl.
CPC .... *A61M 16/0493* (2014.02); *A61M 16/0463* (2013.01); *A61M 16/06* (2013.01); *A61M 16/0816* (2013.01); *A61M 16/10* (2013.01)

(58) Field of Classification Search
CPC .................................................. A61M 16/06
USPC .................. 128/847, 859, 861, 848; 433/80; 600/560
See application file for complete search history.

(56) References Cited

U.S. PATENT DOCUMENTS

| 4,071,026 A * | 1/1978 | Bevins ................... A62B 23/00 128/205.29 |
| 4,495,945 A * | 1/1985 | Liegner ............. A61M 16/0493 128/200.26 |
| 5,884,625 A * | 3/1999 | Hart ........................ A61F 5/566 128/204.18 |
| 8,091,554 B2 * | 1/2012 | Jiang ....................... A61F 5/566 128/200.24 |
| 2012/0234331 A1 * | 9/2012 | Shantha .................. A61F 5/566 128/848 |

* cited by examiner

Primary Examiner — Anna K Kinsaul
Assistant Examiner — Caitlin A Carreiro
(74) Attorney, Agent, or Firm — Larry J. Guffey; Oliver & Grimsley, LLC

(57) ABSTRACT

An improved ventilation device that can be inserted into the mouth of a patient to provide an airway through the oral pharyngeal cavity includes: (a) a mouthpiece having an interior portion that is bounded by top and bottom surfaces, outer and inner semi-elliptically-shaped perimeter surfaces and two end surfaces, wherein: (a1) each of these end surfaces is oriented approximately parallel to the minor axes of the perimeter surfaces, (a2) the outer perimeter surface has a front portion proximate the point where it is intersected by its major axis, (b) top and bottom recesses in the mouthpiece's respective top and bottom surfaces that each are configured to accommodate a patient's respective upper and lower teeth, and (c) an airflow passageway through the mouthpiece's interior portion.

8 Claims, 4 Drawing Sheets

INTERMANDIBULAR/MAXILLARY VENTILATION DEVICE

CROSS-REFERENCE TO RELATED APPLICATION

This application claims the benefit of Provisional Patent Application No. 61/759,601, filed Feb. 1, 2013 by the present inventor. The teachings of this earlier application are incorporated herein by reference to the extent that they do not conflict with the teaching herein.

BACKGROUND OF THE INVENTION

1. Field of the Invention

The present invention generally relates to a surgical device. Specifically, the invention is directed to a ventilation device for human airways that can be rapidly and easily inserted to provide adequate ventilation of a patient's lungs.

2. Description of the Related Art

Resuscitation of a comatose or semi-comatose patient who stops breathing requires the ventilation of the lungs, which is usually fraught with difficulties, often leading to an unsuccessful resuscitation and death. Conventionally, a face mask connected with a manually operated air bag respirator is used with a separate oral airway to provide positive pressure breathing. During this procedure air that is forced by the bag into the space between the mask interior and the patient's face often tends to force the patient's cheeks away from the periphery of the mask, where air that should enter the airway into the patient's lungs, instead leaks out under the mask into the environment.

In addition, partial or complete obstruction of the airway by the patient's tongue, buccal mucosa, teeth, gingiva (gums) and/or lips increases the air leakage between the face mask and the patient's cheeks thereby reducing the ventilation of the lungs. Furthermore, when a patient is able to breathe on his/her own but the patient's breathing effort is reduced by drugs, brain dysfunction, deep sleep, etc. and/or there is partial or complete nasal obstruction, the patient may require a simple oral airway to bypass the anatomical obstructions noted above and allow for less obstructed breathing through the patient's mouth.

Present oral airway devices are placed over the back of the tongue and therefore will stimulate a gag reflex. Patients will either not be able to tolerate this stimulation or it might even cause them to vomit with resultant life threatening aspiration of vomitus. Additionally, hollow, midline, oral devices are specially unstable in the mouth as they are held in place only by a patient's tongue and the roof of one's mouth; thereby making it impractical to attach positive pressure breathing equipment to such devices in order to support respiration. Also, curved midline airways need to be inserted at an angle and might inadvertently push the tongue back into the throat, thereby worsening an airway obstruction. Better devices are required to improve the practice of resuscitation as well as increase the effectiveness of the oral airway. Jiang, U.S. Pat. No. 8,091,554 ('544) shows a device that uses a mouthpiece to close off and remove air from the oral cavity. Its medical objective is to provide a vacuum in the oral cavity that will pull the tongue forward sealing off the mouth allowing for a nasopharyngeal airway for either, physiologic breathing through the nose, or assisted nasal positive pressure breathing. The primary objective of the '544 device is to remove the obstruction caused by the tongue in a human airway related to snoring and/or obstructive sleep apnea. The '554 device's hollow member applies suction out of the front of the device in order to pull the tongue forward via multiple openings along an inner surface of the device.

The '554 patent does not provide a clear airway through the oral pharyngeal cavity for either physiologic breathing through the mouth or assisted oral positive pressure breathing. For an effective clear airway through the oral pharyngeal cavity, a hollow member of such a device must allow air to flow freely in and out of the openings at the front and rear of such a device when it is inserted into a patient's mouth.

When patients are semi-comatose or extremely relaxed or sedated, breathing through their mouth and nose may become partially or completely obstructed because of the relaxed tissues of their mouth, including the tongue. The '554 device seals a patient's mouth with a vacuum to pull the tongue forward to theoretically improve the airway from the nose through the pharynx and thereby allow improved airflow through the nose into the lungs. However, if there is any degree of nasal obstruction in a patient using the '544 device, its anticipated improved ventilation can quickly diminish even if positive pressure breathing is applied to the nose.

Thus, there continues to exist a need for an improved ventilation device that can be inserted into a patient's mouth to provide an airway through the oral pharyngeal cavity to provide adequate ventilation for a patient's lungs.

SUMMARY OF THE INVENTION

Recognizing the need for an improved ventilation device that can be inserted into the mouth of a patient to provide an airway through the oral pharyngeal cavity of the patient, the present invention is generally directed to overcoming the problems and disadvantages exhibited by prior devices due to airflow obstructions created by the patient's tongue, buccal mucosa, teeth and gums. In addition, the present device is stabilized between a patient's upper and lower teeth or gums and thereby provides a stable platform which can be connected to a source of positive pressure ventilation.

The present invention is a ventilation device that provides a clear airway through the oral cavity for either physiologic breathing through the mouth or assisted oral positive pressure breathing. One variant of the ventilation device of the present invention includes: (a) a mouthpiece having an interior portion that is bounded by top and bottom surfaces, outer and inner semi-elliptically-shaped perimeter surfaces and two end surfaces, wherein: (a1) the outer and inner perimeter surfaces are each defined by their major and minor axes, (a2) each of these end surfaces are oriented approximately parallel to the minor axes of the mouthpiece's perimeter surfaces, (a3) the outer perimeter surface has a front portion proximate the point where it is intersected by its major axis, (b) a top recess in the mouthpiece top surface between its perimeter surfaces that has a configuration adapted to accommodate the upper teeth of the patient in this top recess, (c) a bottom recess in the mouthpiece bottom surface between its perimeter surfaces that has a configuration adapted to accommodate the lower teeth of the patient in this bottom recess, and (d) an airflow passageway through the mouthpiece's interior portion that has a front opening, that intersects the outer perimeter's front portion, and two rear openings which each intersect one of the mouthpiece's end surfaces.

Another variant of the ventilation further includes two nozzles, each of which has an inlet and an exit and wherein these inlets connect to one of the end surfaces' rear openings. These nozzles have a configuration adapted to direct airflow from the rear opening so that the airflow will avoid any airflow obstruction caused by the patient's tongue and soft tissues in the vicinity of a nozzle exit.

Yet another variant of the ventilation further includes an airflow inlet means that connects to the airflow passage front opening and has a configuration adapted to aid in enabling an external, positive pressure airflow source to be connected to the mouthpiece.

Positive pressure ventilation applied to the mouthpiece's airflow inlet means may be achieved directly or in combination with a respiratory mask. Use of such a mask helps to prevent intended ventilation airflow from escaping the nose and mouth. Airflow from this mouthpiece's nozzle exits is oriented to extend away from the patient's teeth and buccal mucosa and towards a patient's tongue and the posterior oropharynx.

Thus, there has been summarized above (rather broadly and understanding that there are other preferred embodiments which have not been summarized above) the present invention in order that the detailed description that follows may be better understood and appreciated.

DESCRIPTION OF THE PREFERRED EMBODIMENT

Figure 1:
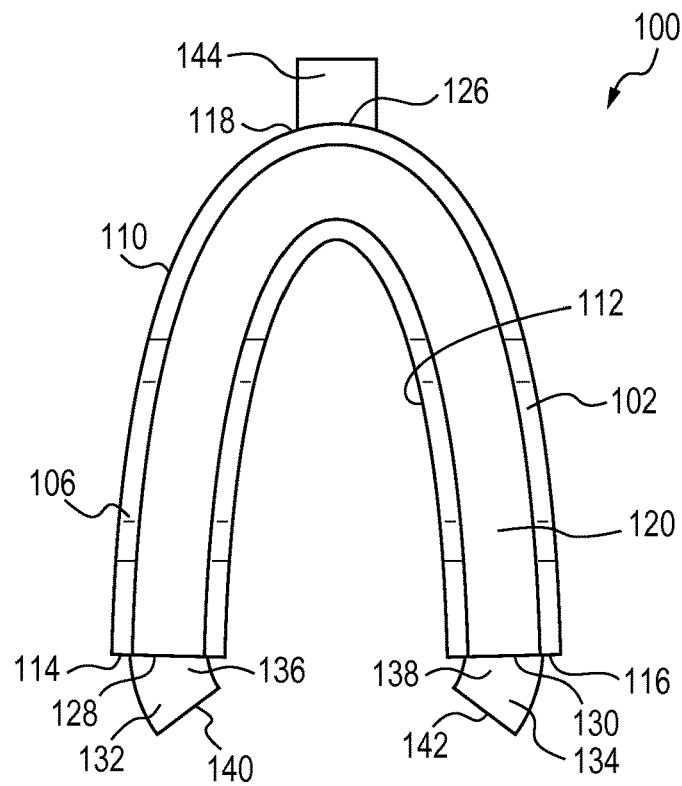
FIG. 1 is a top view of a preferred embodiment of the present invention.
Figure 2:
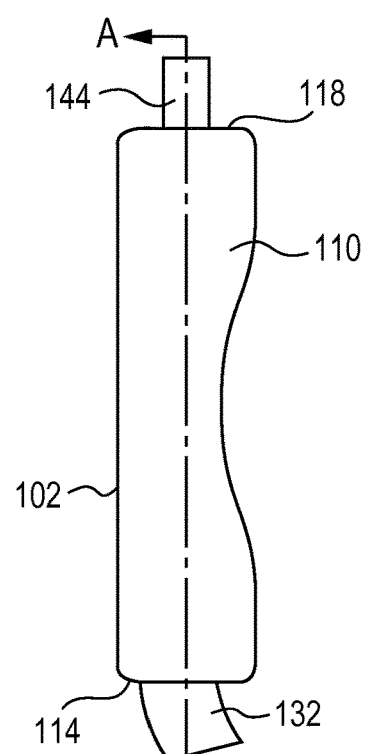
FIG. 2 is a side view of the embodiment shown in FIG. 1.
Figure 3:
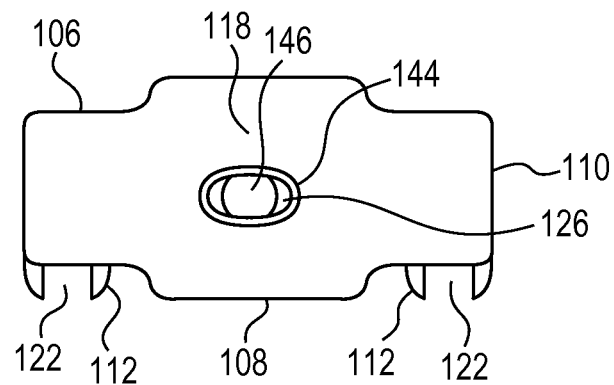
FIG. 3 is a front view of the embodiment shown in FIG. 1.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention generally relates an improved ventilation device that can be inserted into the mouth of a patient to provide an airway through the oral pharyngeal cavity of the patient. In a preferred embodiment, it includes a mouthpiece that holds a patient's mouth open while also functioning as an airway to provide airflow to a patient's unobstructed sulcus—which is formed by the angle of the open mandible and maxilla behind the posterior molar teeth and adjacent to the back of the tongue, where airflow over the tongue to the posterior oropharynx can more easily travel into the lungs. The present invention's location between the mandible (lower teeth) and the maxilla (upper teeth) not only holds the mouth in an open position, it also provides a spatially stabile airway between these two bony surfaces.

A preferred embodiment of the present invention 100 includes: a mouthpiece 102 having an approximately, U-shaped, inner or interior portion 104 that is bounded by approximately, U-shaped, top 106 and bottom 108 surfaces, outer 110 and inner 112 semi-elliptically-shaped perimeter surfaces and two end or rear surfaces 114, 116. See FIGS. 1-4. Since these perimeter surfaces are semi-elliptically-shaped, they can each be defined by their major and minor axes—which in FIG. 1's top view implies that these major axes run vertically to divide in half the mouthpiece, while the minor axes in FIG. 1 run horizontally and are located at approximately at the rear boundary of this mouthpiece.

Each of these end or rear surfaces 114, 116 are oriented approximately parallel to the minor axes of the mouthpiece's perimeter surfaces 110, 112 so as to intersect and connect them. See FIG. 2. The mouthpiece's outer perimeter surface has a front portion 118 that is proximate the point where it is intersected by its major axis.

The mouthpiece's top 106 and bottom 108 surfaces each have a recess, i.e. a top 120 and a bottom 122 recess, between its perimeter surfaces 110, 112 that has a configuration adapted to accommodate in these recesses 120, 122 the adjoining upper or lower teeth or gums of a patient.

Figure 5:
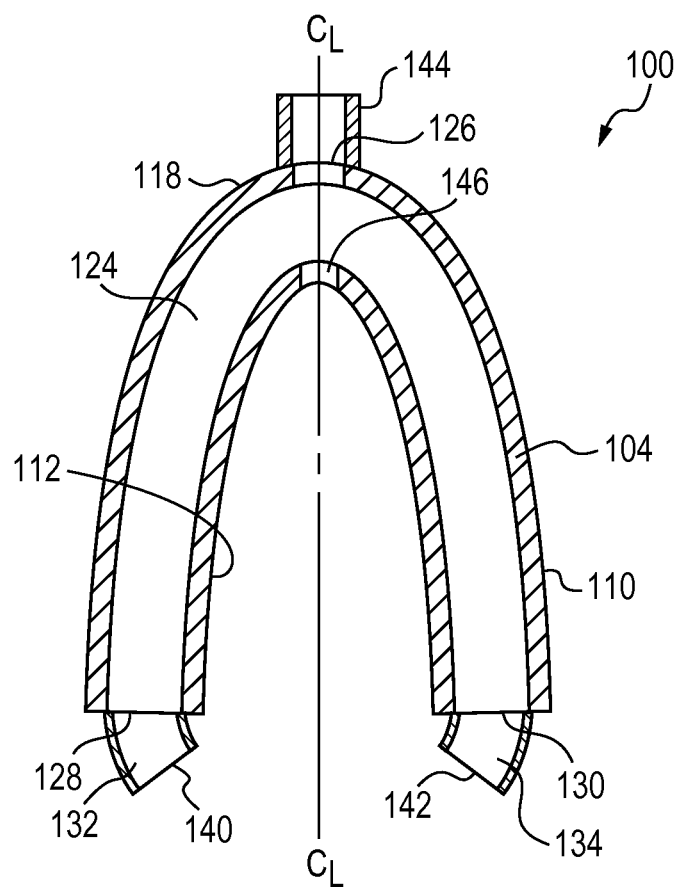
FIG. 5 is a cross-sectional view taken along the direction of A-A shown in FIG. 2.

This mouthpiece also has an airflow passageway 124 through it's interior portion that has a front 126 opening that intersects the outer perimeter's front portion 118 and two rear openings 128, 130 which each intersect one of the mouthpiece's two end surfaces 114, 116. See FIG. 5. A nozzle 132, 134, each of which has an inlet 136, 138 and an exit 140, 142, connects to each of the end surfaces' rear openings. Each of these nozzles has a configuration adapted to direct airflow from the rear opening so that it will avoid any obstruction caused by the patient's tongue and soft tissues in the vicinity of a nozzle's exit.

Figure 4:
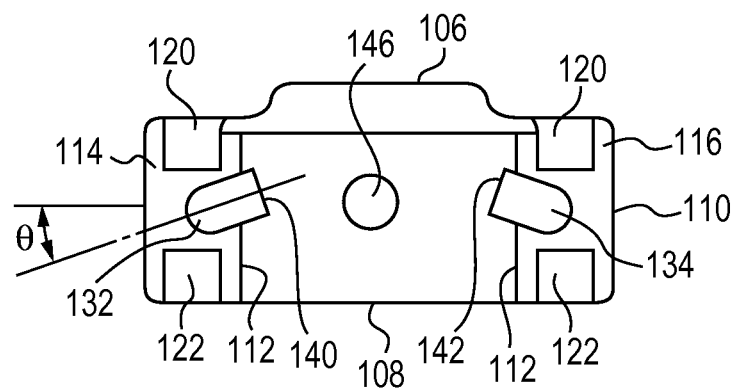
FIG. 4 is a rear view of the embodiment shown in FIG. 1.

As illustrated in FIG. 4, each nozzle exit 140, 142 is situated within the mandibular maxillary sulcus, adjacent and angled as shown by angle θ, with respect to the orientation of the tongue, thus avoiding obstruction by the tongue or other soft tissues.

Figure 6:
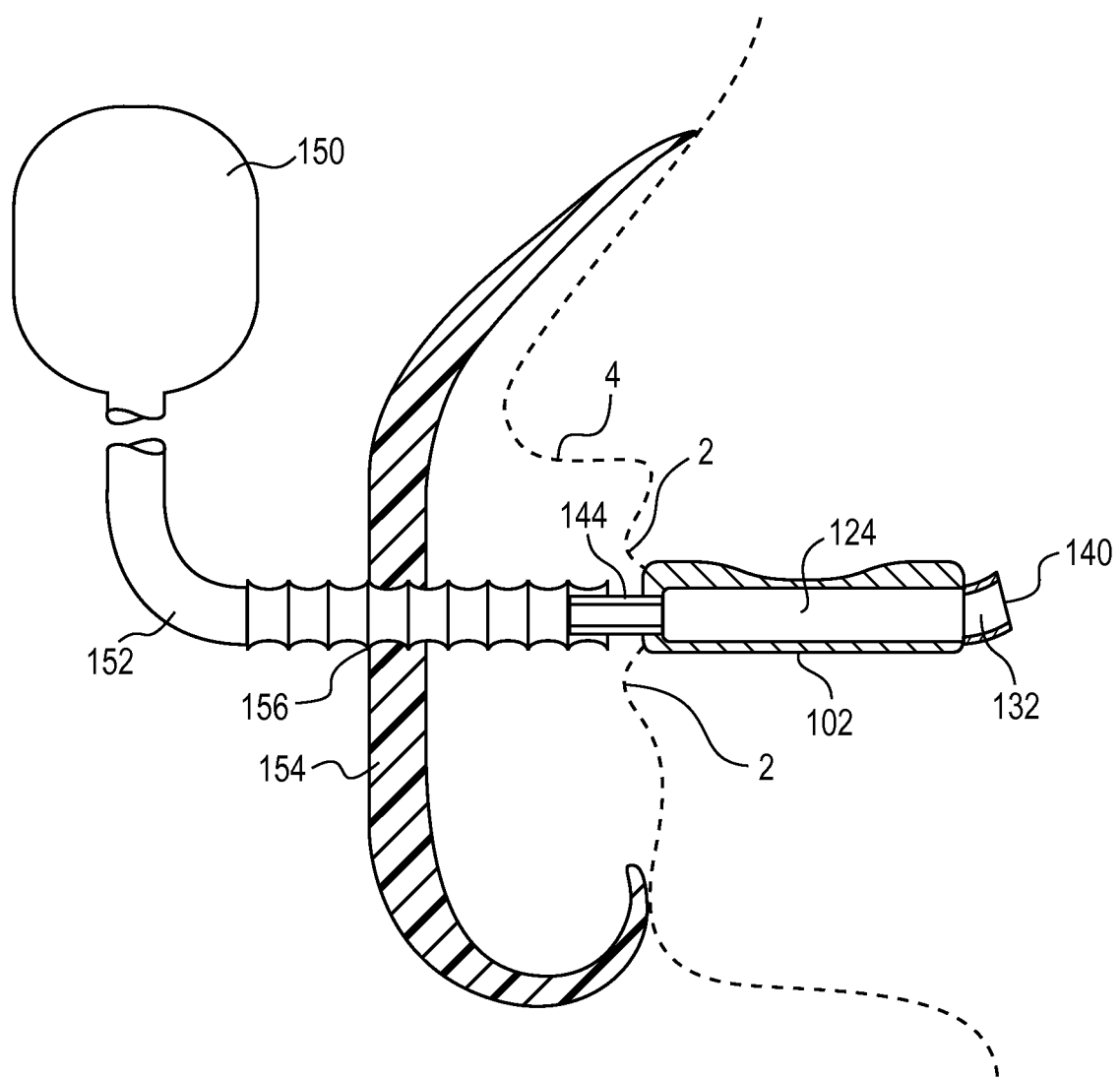
FIG. 6 is a cross-sectional view of the mouthpiece of the present invention being used in conjunction with a facial respiratory mask and an external, positive-pressure, airflow source or ventilation device.

This ventilation device may also include an airflow inlet means or receiving nozzle 144 that connects to the airflow passage front opening 126 and has a configuration adapted to aid in enabling a positive pressure airflow source 150 with a suitable connecting link 152 to be connected to the mouthpiece. As shown in FIG. 6, this receiving nozzle 144, in association with the outer perimeter surface 110, behind the patient's lips 2, is in fluid communication with the airflow passageway's left and right portions to allow air to flow from a source, external to the lips, through the receiving nozzle 144, the passageway 124 and to the two opposing nozzle exits 140, 142 that are situated in the rear of a patient's mouth when the device is in use.

For those patients who are unresponsive and cannot swallow their own oral secretions, a suction opening 146 has been provided through the inner perimeter surface 112 at a point proximate the mouthpiece's centerline. See FIG. 5. The purpose of this opening 146 is to allow for the insertion of a suction member through the front opening 126 of the mouthpiece's airflow passageway and through this suction opening 146 so as to gain access to the portion of a patient's mouth that is behind this mouthpiece. Suctioning through this opening 146 into the posterior oropharynx will allow for the removal of secretions that might otherwise be aspirated into the patient's lungs.

This suction opening 146 will not interfere with the ventilation function of this airflow device. Although this opening 146 may be partially or completely obstructed by the tongue, such an obstruction can be easily overcome by using a semi-rigid, suction catheter for any necessary suctioning task. When there is no suctioning being performed and white the patient is breathing or being ventilated using positive air pressure, some air may pass through this suction opening 146 and flow around and over the tongue down into the lungs. Such an airflow will supplement the intended function of the present invention, but, when the tongue partially or completely obstructs this suction opening 146, air will then flow through the device's right and left airflow passageways 124 and out through the two, non-tongue-obstructed rear openings 128, 130 thereby allowing the device to function in its intended manner.

In a fully comatose or obtunded patient or a patient without any respiratory effort such as a patient in cardio-respiratory arrest, the ventilation device of the present invention can apply positive pressure to the front opening of a mouthpiece that may or may not include a facial respiratory mask 154. Such a facial respiratory mask will typically have an opening 156 that allows a connecting link 152 from an external positive pressure airflow source 150 to be connected to the mouthpiece's airflow inlet means 144. The mouthpiece and mask when used together serve to prevent any intended ventilation air from escaping through a patient's nose 4 and mouth.

The device of the present invention can also function with a potentially complete nasal obstruction by providing an open oral airway where airflow would be presented to the back of the oral cavity and tongue, such that airflow from each nozzle exit is oriented to extend away from the patient's teeth and over a patient's tongue to the posterior oropharynx in order that air is in fluid communication with the lungs.

This device also allows airflow between the lips and upper and lower teeth and gums as well as bypassing the buccal mucosa without stimulating a gag reflex at the back of the throat as typically occurs with the traditional, curved midline airway devices that ride over the back of the tongue. The mouthpiece of the present invention requires a sufficiently large opening at the front and rear of the device, as well as a sufficiently large space between the mandible and maxilla, to allow for life supporting ventilation both throughout inhalation and expiration via the oral cavity.

The present invention is faster and easier to insert into the mouth because it does not have to ride over and curve down over the posterior tongue as occurs with the traditional, curved midline oral airway. It therefore does not need to be angled up or down during insertion but can be pushed straight into the mouth and because it avoids any contact with the tongue, it will not accidentally push the tongue posteriorly thereby unintentionally closing off the airway. This simple, rapid, straight insertion technique therefore allows this device to work more efficiently when used in combination with a respiratory mask.

The top and bottom surfaces of the device, upon which the upper and lower teeth or gingiva rest, can be either parallel to one another or angled to one another with the anterior portion forming the open side of the angle.

The foregoing is considered as illustrative only of the principles of the present invention. Further, since numerous modifications and changes will readily occur to those skilled in the art, it is not desired to limit the invention to the exact construction and operation shown and described herein. Accordingly, all suitable modifications and equivalents may be resorted to, falling within the scope of the invention that is hereafter set forth in the claims to the invention.

I claim:

1. A ventilation device that is configured to be inserted into the mouth of a patient so that the device is capable of providing an airway through the oral pharyngeal cavity of said patient while avoiding airflow obstructions due to the tongue, buccal mucosa, teeth, including molar teeth, and gums of said patient, said device comprising:
    a mouthpiece having a U-shaped, interior portion that is bounded by U-shaped, top and bottom surfaces that are oriented approximately parallel to one another, outer and inner perimeter surfaces, with each of said outer and inner perimeter surfaces having a front portion, that are each oriented approximately perpendicular to said U-shaped, top and bottom surfaces and two, rear, free end surfaces, wherein said front portion of said outer and inner perimeter surfaces is each defined as the portion of either perimeter surface that is approximately equal distance from each of said rear, free end surfaces,
    a top recess in said U-shaped, top surface that has a configuration adapted to accommodate the upper teeth of said patient in said U-shaped, top recess,
    a bottom recess in said U-shaped, bottom surface that has a configuration adapted to accommodate the lower teeth of said patient in said U-shaped, bottom recess,
    wherein said mouthpiece is configured to locate each of said rear, free end surfaces behind the molar teeth of said patient and at a furthest point where said mouthpiece penetrates into the oral pharyngeal cavity of said patient, and with each of said rear, free end surfaces oriented so that a perpendicular from each of said rear, free end surfaces is directed approximately parallel to the adjacent buccal mucosa of said oral pharyngeal cavity of a patient,
    four openings in said U-shaped, interior portion, including an outer, front opening that intersects said front portion of said outer perimeter surface, a single, approximately round, suction opening in said inner perimeter surface, and two rear openings, each of which intersects one of said two, rear, free end surfaces,
    wherein said outer, front opening and two rear openings are each configured to enable said U-shaped, interior portion to act as an airflow passageway to direct the air entering said outer front opening to a point that is both proximate the buccal mucosa of said oral pharyngeal cavity and also the furthest to which said mouthpiece penetrates into the oral pharyngeal cavity of a patient,
    wherein each of said two rear openings is further configured to direct the air flowing from said rear opening so that said air flows approximately parallel to the adjacent buccal mucosa of said oral pharyngeal cavity, and
    wherein said single, approximately round suction opening having a center point and an orientation such that a perpendicular line located at said center point and extending towards said outer perimeter surface passes through said front opening so as to enable said suction opening and said front opening to be directly aligned to provide a substantially straight-line, suction passageway that allows for the removal of secretions from the posterior oropharynx of said patient.

2. The ventilation device as recited in claim 1, further comprising: an airflow inlet means that connects to said outer, front opening and has a configuration adapted to aid in enabling an exterior positive pressure airflow source to be connected to said mouthpiece.

3. The ventilation device as recited in claim 2, further comprising: a pair of nozzles, each having an inlet and an exit and with said inlet connecting to one of said rear openings and with each of said nozzles having a configuration adapted to direct airflow from said rear openings so as to avoid any obstruction caused by said patient's tongue and soft tissues in the vicinity of said nozzle exit.

4. The ventilation device as recited in claim 3, further comprising:
- a facial respiratory mask having an opening that allows for an external positive pressure airflow source to be connected to said airflow inlet means of said mouthpiece and wherein said mask has a configuration adapted to help prevent any intended ventilation air from escaping through the nose or mouth of said patient.

5. The ventilation device as recited in claim 2, further comprising: a facial respiratory mask having an opening that allows for an external positive pressure airflow source to be connected to said airflow inlet means of said mouthpiece and wherein said mask has a configuration adapted to help prevent any intended ventilation air from escaping through the nose or mouth of said patient.

6. The ventilation device as recited in claim 1, further comprising: a pair of nozzles, each having an inlet and an exit and with said inlet connecting to one of said rear openings and with each of said nozzles having a configuration adapted to direct airflow from said rear openings so as to avoid any obstruction caused by said patient's tongue and soft tissues in the vicinity of said nozzle exit.

7. The ventilation device as recited in claim 6, further comprising: a facial respiratory mask having an opening that allows for an external positive pressure airflow source to be connected to said airflow inlet means of said mouthpiece and wherein said mask has a configuration adapted to help prevent any intended ventilation air from escaping through the nose or mouth of said patient.

8. The ventilation device as recited in claim 1, further comprising: a facial respiratory mask having an opening that allows for an external positive pressure airflow source to be connected to said airflow inlet means of said mouthpiece and wherein said mask has a configuration adapted to help prevent any intended ventilation air from escaping through the nose or mouth of said patient.

* * * * *